United States Patent
Reichel et al.

(10) Patent No.: US 10,150,934 B2
(45) Date of Patent: Dec. 11, 2018

(54) METHOD FOR THE PURIFICATION OF FATTY ACID AKLYL ESTERS

(71) Applicant: BDI-BIOENERGY INTERNATIONAL AG, Grambach (AT)

(72) Inventors: Martin Reichel, Graz (AT); Robert Raudner, Köflach (AT)

(73) Assignee: BDI-BIOENERGY INTERNATIONAL AG, Grambach (AT)

( * ) Notice: Subject to any disclaimer, the term of this patent is extended or adjusted under 35 U.S.C. 154(b) by 0 days.

(21) Appl. No.: 15/535,195

(22) PCT Filed: Nov. 30, 2015

(86) PCT No.: PCT/EP2015/078085
§ 371 (c)(1),
(2) Date: Jun. 12, 2017

(87) PCT Pub. No.: WO2016/091640
PCT Pub. Date: Jun. 16, 2016

(65) Prior Publication Data
US 2017/0349857 A1    Dec. 7, 2017

(30) Foreign Application Priority Data
Dec. 11, 2014    (EP) .................................... 14197324

(51) Int. Cl.
*C11B 3/14*    (2006.01)
*C07C 67/54*    (2006.01)
(Continued)

(52) U.S. Cl.
CPC ................ *C11B 3/14* (2013.01); *B01L 3/10* (2013.01); *C07C 67/54* (2013.01); *C10L 1/026* (2013.01);
(Continued)

(58) Field of Classification Search
CPC ..... B10D 13/10; C10L 2290/543; C10L 1/19; C10L 2200/0476; C11B 3/12; C11B 3/14; B01D 3/10; C07C 67/54
See application file for complete search history.

(56) References Cited

U.S. PATENT DOCUMENTS

| | | | |
|---|---|---|---|
| 2011/0197497 A1* | 8/2011 | Jiang ..................... | C10L 1/026 44/307 |
| 2013/0212933 A1* | 8/2013 | Morgan ................... | C10L 1/19 44/388 |

FOREIGN PATENT DOCUMENTS

| WO | WO9924387 | 5/1999 | |
|---|---|---|---|
| WO | WO2004083350 | 9/2004 | |
| WO | WO 2004083350 | * 9/2004 | ................ C10L 1/02 |

OTHER PUBLICATIONS

WO 2004083350; BDI Anlagenbau GES M B H [AT], Purified low sulfur-containing fat acid alkyl ester and method for the production thereof, English translation, 6 pages (Year: 2004).*

(Continued)

*Primary Examiner* — Yate' K Cutliff
(74) *Attorney, Agent, or Firm* — Workman Nydegger

(57) ABSTRACT

In a process for purifying fatty acid alkyl esters, particularly methyl and ethyl esters, by means of vacuum distillation in a distillation column, water or steam is introduced into the distillation column and, during distillation, brought into contact with the fatty acid alkyl esters in the gas phase. This results in a significant reduction in the sulphur content and in the acid number of the fatty acid alkyl ester.

12 Claims, 2 Drawing Sheets

(51) Int. Cl.
*B01L 3/10* (2006.01)
*C10L 1/02* (2006.01)
(52) U.S. Cl.
CPC . *C10L 2200/0476* (2013.01); *C10L 2290/543* (2013.01)

(56) References Cited

OTHER PUBLICATIONS

International Preliminary Report on Patentability cited in PCT/EP2015/078085 dated Jun. 13, 2017.

* cited by examiner

METHOD FOR THE PURIFICATION OF FATTY ACID AKLYL ESTERS

The invention relates to a process for purifying fatty acid alkyl esters, particularly methyl and ethyl esters, by means of vacuum distillation in a distillation column.

For the production of biodiesel (fatty acid methyl ester=FAME) according to European standard EN 14214, vegetable oils or waste products such as, e.g., used cooking oils, cleaved fatty acids or animal fats are used in an industrial scale. In particular animal fat of category 1, a high-risk material in regard to the contamination with TSE (Transmissible Spongiforme Enzephalopathy, e.g., BSE), may be converted into a valuable fuel through chemical conversion into a fatty acid methyl ester with subsequent distillation.

An essential disadvantage of these starting materials, in particular of the waste materials cleaved fatty acids and animal fat, however, lies in the high concentration of sulphur thereof, which in the case of cleaved fatty acids has its origin in the work-up process and in the case of animal fats in the starting material of animal origin. In the finished product, i.e., biodiesel, the sulphur content is regulated according to EN 14214 to be at the most 10 ppm. It has, however, been shown that even following transesterification there may still be detectable sulphur compounds in the ester, so that the limit value of 10 ppm is occasionally exceeded by far. Washing the raw ester that is usually performed and the subsequent distillation likewise lead only to a moderate reduction in the sulphur content so that the starting material has its limits in regard to the sulphur concentration thereof.

In order to enable the processing of raw materials having a higher sulphur content, distillation has to be n overdimensioned and/or run at a lower load or higher residue rate, respectively, which, however, will lead to higher operational costs, poorer yield and low through-put and will require higher investment.

In order to reduce the concentration of sulphur in the biodiesel, there have been proposed various processes:

According to U.S. Pat. No. 8,585,901, the raw materials for the biodiesel production are treated with sulphur oxidizing microbes, e.g., *Thiobacillus* sp. and *Alcaligenes* sp., in order to reduce the sulphur content prior to esterification.

WO 2004/083350 teaches a process wherein the fatty acid alkyl ester obtained is treated with a basic medium, e.g., KOH or CaOH.

According to U.S. Pat. No. 6,242,620, the esters are purified using an aqueous alkaline solution and silica gel.

In US 2013/0212933, there is described a process for the production of low-sulphur biodiesel made from animal or vegetable oils, in which the raw materials are subjected to esterification by means of reactive distillation, wherein in the reactive distillation a sulphonic acid-containing ion exchanger is used as a catalyst.

A similar process is also described in WO 2009/018390, wherein, in contrast to US 2013/0212933, a vacuum distillation is carried out before the esterification in order to pre-purify the free fatty acids. Following the esterification, the liquid raw product may be further subjected to an additional purification step, e.g., a distillation, an adsorption or a reboiled stripping.

In the already known processes, a reduction of the sulphur content is achieved, however, this will mostly be insufficient or will require additional effort in order to enable the use of heavily sulphurous and, thus, cost efficient starting materials.

The invention thus has as its object to provide a process for purifying fatty acid alkyl esters, which enables the use of raw materials having a high amount of sulphur while meeting the sulphur limit value of 10 ppm according to EN 14214, without disadvantageous processing or additional purification steps being required.

According to the invention, with a process of the initially mentioned type this object is achieved in that water or steam is introduced into the distillation column and, during distillation, is brought into contact with the fatty acid alkyl esters in the gas phase.

As residual humidity in the distillation material has disadvantageous effects on the distillation in general, in particular the vacuum system thereof, the water is usually removed from the fatty acid alkyl esters before distillation by means of suitable measures, e.g., a drying column. Surprisingly, it has been found, however, that a significant reduction in the sulphur content occurs if the fatty acid alkyl ester, this is, e.g., the raw biodiesel is brought into contact with steam during distillation, that is, when it is in the gas phase. It has been shown that those sulphur compounds in particular that cannot be further separated by means of conventional distillation may be removed.

Another surprising advantage of the process according to the invention is that, apart from the reduction in the sulphur content, there is achieved also a reduction in the neutralization number (=mg of potassium hydroxide necessary to neutralize the acids contained in 1 g of the sample). In particular for biodiesel, a low neutralization number or acid number (limit value according to EN 14214: 0.5 mg KOH/g), that is, a low content of free fatty acids, is desirable, as acidic compounds in the fuel will lead to corrosion, wear and formation of residues in the engine.

In order to achieve the required reduction of sulphur, water or steam is introduced in an amount of preferably 0.5-10.0 kg/t of fatty acid alkyl ester, more preferably 2.0-5.0 kg/t of fatty acid alkyl ester, into the distillation column. Below 0.5 kg/t, an economically reasonably purifying effect does not take place any more, whereas above 10.0 kg/t there is no notable increase of the purification effect but rather, due to the introduction of water, an operational impairment of the vacuum distillation.

According to a preferred embodiment, the water or steam is supplied to a part of the distillation residue, which is returned into the distillation column, so that the water is introduced together with this distillation residue into the distillation column.

According to a further preferred embodiment, the water or steam is supplied to the fatty acid alkyl esters to be purified and is introduced together with these into the distillation column.

A further preferred embodiment is characterized in that the water or steam is fed directly into the distillation column.

Even though the addition of water or steam may occur at any point before the actual distillation, that is, the separation of the highly volatile components, the supply in the lower part of the distillation column, e.g., in the falling film evaporator, will be especially advantageous because as a result of this there will occur a particularly long contact between water/steam and the gaseous ester phase.

According to a further preferred embodiment the highly volatile components including water will be removed from the fatty acid alkyl esters prior to distillation. For this purpose, a flash evaporation is preferably carried out.

By this measure, it is possible to induce constant conditions in the subsequent vacuum distillation, as, by a previous separation of residual humidity from the raw ester, a quantity-controlled addition of water or steam becomes possible in a simple way.

Furthermore, this measure has positive effects on the subsequent vacuum distillation, as, due to the removal of the highly volatile components such as, e.g., methanol, still present in the ester raw product, the dimensioning of the vacuum systems may be reduced.

The vacuum distillation is preferably performed at a pressure of <10 mbar, preferably <3 mbar. The preferred temperature for the vacuum distillation is 100-260° C., preferably 140-200° C.

The vacuum distillation may be realized in a single step, e.g. by means of short-way distillation, or in multiple steps via rectification. In any case, however, it is advantageous, when adding water or steam, to take care that the contact times between water and ester product in the gas phase are being maximized.

The invention is subsequently explained in greater detail by way of an example as well as the drawing.

EXAMPLES

Figure 1:
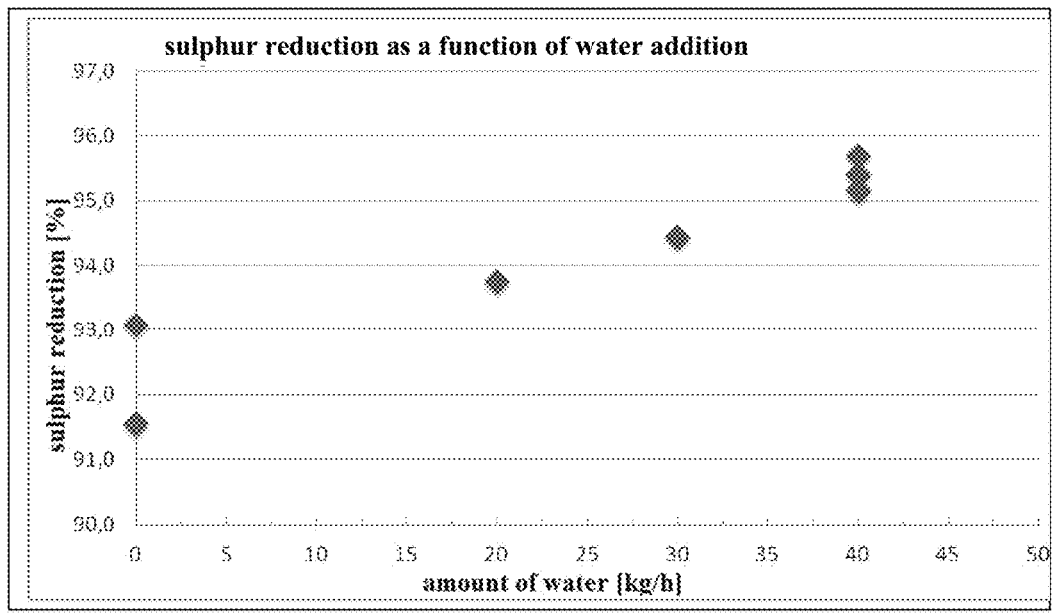
FIG. 1 shows a graphical illustration of the sulphur reduction as a function of the amount of water added in a vacuum distillation according to an embodiment of the invention.
Figure 2:
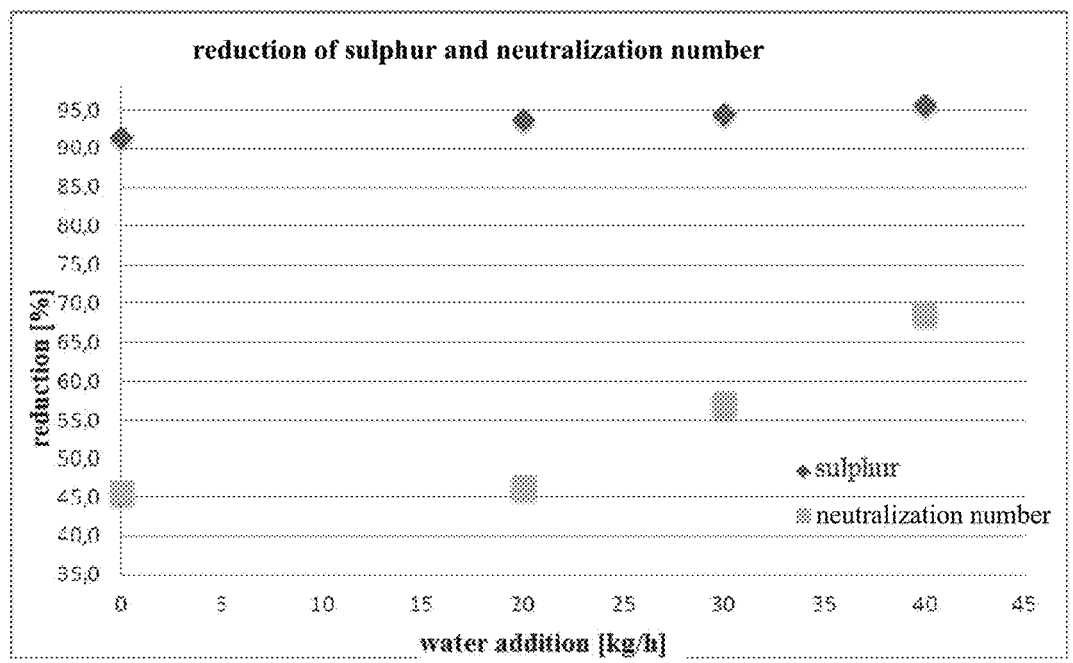
FIG. 2 shows a graphical illustration of the reduction of sulphur as well as of the acid number as a function of the amount of water added in a vacuum distillation according to an embodiment of the invention.
Figure 3:
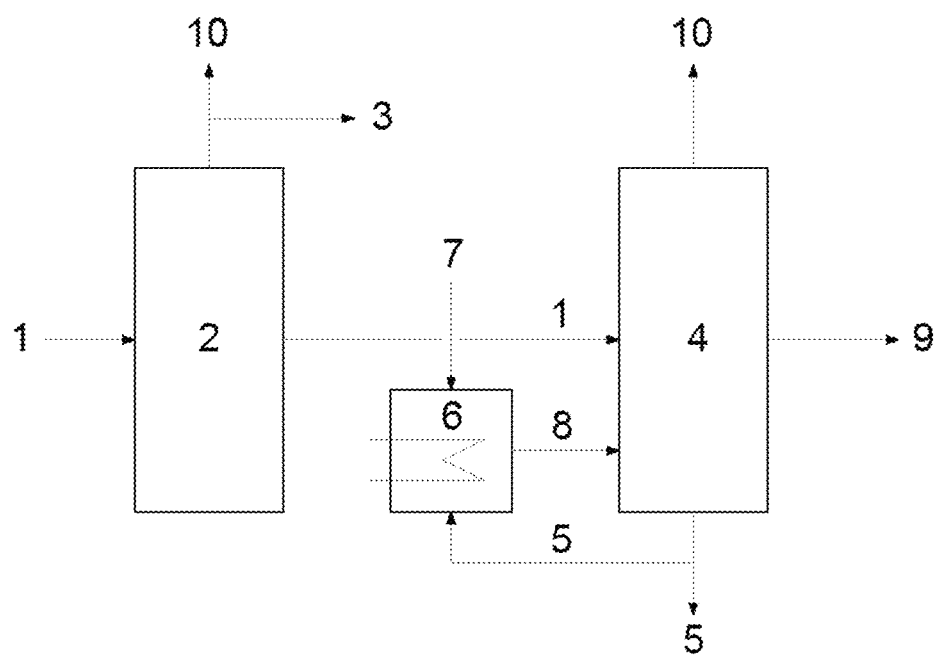
FIG. 3 shows a block diagram of an embodiment of the process according to the invention.

The effects of the introduction of water or steam into the distillation column in order to bring into contact the crude biodiesel in the gas phase with water or steam, respectively, during vacuum distillation were investigated.

Before the start of the study, the operational parameters such as mass balance, reflux rates, supply flows, etc. of the distillation column (rectification column) were determined. After setting constant conditions, samples of the starting product or the supply flow, respectively, and of the distillate were taken and analysed in regard to the sulphur content as well as the neutralization number thereof.

In the first step, the crude biodiesel 1 was freed from highly volatile substances 3 including water in a flash column 2 and subsequently fed into the distillation column 4. The mean supply rate from the flash column 2 to the distillation column 4 during the trials was 19.5 t/h. The pressure or the vacuum, respectively, at the top of the column was between 1.0 and 3.1 mbar. The mean distillation residue rate of the distillation system was kept at 5.4%. Due to the expected increase of the steam pressure in the distillation column there was set a higher sump temperature (184° C.-189° C.) in order to maintain a distillation residue rate as in normal operation (i.e., without addition of water/steam).

The energy necessary for distillation was supplied via a sump circulation flow. In this process, a part of the distillation residue 5 withdrawn from the column sump was heated in a heat exchanger 6. In the heat exchanger 6, water 7 was added as well and thereby supplied to the part of the distillation residue 5 to be returned into the column. The heated mixture 8 of distillation residue 5 and water 7 then was introduced into the distillation column 4, in which, during distillation, a close contact between water or steam, respectively, and the gaseous crude biodiesel 1 occurred.

The purified biodiesel 9 was withdrawn from the distillation column 4 and analysed. The highly volatile sulphur compounds as well as the water introduced into the column were removed by the vacuum system 10. The essential amount of the "washed-out" sulphur was withdrawn from the column sump along with the distillation residue 5 and then discharged from the sump circulation flow.

Table 1 shows the results for normal operation (experiment no° 9A) as well as for the introduction of various amounts of water into the distillation column.

TABLE 1

| exp. no° | water addition [kg/h] | water addition [kg H$_2$O/t of ester] | sulphur content (starting product) [ppm] | sulphur content (after distillation) [ppm] | sulphur reduction [%] |
|---|---|---|---|---|---|
| 9A | 0 | 0 | 130 | 11 | 91.5 |
| 14 | 20 | 1.08 | 128 | 8 | 93.8 |
| 11 | 30 | 1.54 | 126 | 7 | 94.4 |
| 8 | 40 | 2.22 | 152 | 7 | 95.4 |
| 9 | 40 | 2.34 | 124 | 6 | 95.2 |
| 10 | 40 | 2.05 | 139 | 6 | 95.7 |

Table 2, apart from results for the sulphur content, indicates the results of the acid number analysis.

TABLE 2

| exp. no° | water addition [kg/h] | acid number (starting product) [mg KOH/g ester] | acid number (after distillation) [mg KOH/g ester] | acid number reduction [%] |
|---|---|---|---|---|
| 9A | 0 | 1.03 | 0.56 | 45.6 |
| 14 | 20 | 0.97 | 0.52 | 46.4 |
| 11 | 30 | 0.91 | 0.39 | 57.1 |
| 10 | 40 | 1.22 | 0.38 | 68.9 |

The results show that the introduction of water/steam into the distillation column will lead to a significant improvement. In spite of the required higher evaporation temperature in the column sump due to the higher system pressure, it was possible to notably reduce the sulphur content and, surprisingly, also the neutralization number of the biodiesel.

The invention claimed is:

1. A process for purifying fatty acid alkyl esters, comprising:
   distilling fatty acid alkyl esters by vacuum distillation in a distillation column;
   introducing water or steam into the distillation column in an amount of 0.5-10.0 kg/t of fatty acid alkyl ester; and
   during distillation, contacting the fatty acid alkyl esters with the water or steam in the gas phase.

2. A process according to claim 1, wherein a distillation residue is produced and a part is returned into the distillation column and the water or steam is supplied to the part of the distillation residue to be returned and introduced together with said part into the distillation column.

3. A process according to claim 1, wherein the water or steam is supplied to the fatty acid alkyl esters to be purified and introduced together with said esters into the distillation column.

4. A process according to claim 1, wherein the water or steam is fed directly into the distillation column.

5. A process according to claim 1, wherein highly volatile components including water are removed from the fatty acid alkyl esters prior to distillation.

6. A process according to claim 5, wherein highly volatile components including water are removed through flash evaporation.

7. A process according to claim 1, wherein the vacuum distillation is carried out at a pressure of <10 mbar.

8. A process according to claim 1, wherein the vacuum distillation is carried out at a temperature of 100-260° C.

9. A process according to claim 1, wherein the fatty acid alkyl esters comprise at least one of methyl fatty acid esters or ethyl fatty acid esters.

10. A process according to claim 1, wherein the water or steam is introduced in an amount of 2.0-5.0 kg/t of fatty acid alkyl ester into the distillation column.

11. A process according to claim 1, wherein the vacuum distillation is carried out at a pressure of <3 mbar.

12. A process according to claim 1, wherein the vacuum distillation is carried out at a temperature of 140-200° C.

\* \* \* \* \*